United States Patent
Pensler et al.

(10) Patent No.: US 6,508,817 B1
(45) Date of Patent: Jan. 21, 2003

(54) FINGER TISSUE EXPANDER

(75) Inventors: Jay M. Pensler, Chicago, IL (US); Norris C. Carroll, Sarasota, FL (US); Brian S. Schumacher, Jacksonville, FL (US)

(73) Assignee: Walter Lorenz Surgical, Inc., Jacksonville, FL (US)

( * ) Notice: Subject to any disclaimer, the term of this patent is extended or adjusted under 35 U.S.C. 154(b) by 0 days.

(21) Appl. No.: 09/375,655

(22) Filed: Aug. 17, 1999

(51) Int. Cl.$^7$ ............................................. A61F 5/04
(52) U.S. Cl. ........................................... 606/57; 606/90
(58) Field of Search ................................. 606/216, 190, 606/193, 196–197, 57, 90, 105; 600/232, 215, 235; 128/20

(56) References Cited

U.S. PATENT DOCUMENTS

| 4,573,459 A | * | 3/1986 | Litton | |
| 4,747,395 A | * | 5/1988 | Brief | 128/20 |
| 5,795,291 A | * | 8/1998 | Koros et al. | 600/232 |

FOREIGN PATENT DOCUMENTS

SU 1456108 * 2/1989 ........... A61B/17/02

* cited by examiner

*Primary Examiner*—Cary E. O'Connor
(74) *Attorney, Agent, or Firm*—Harness, Dickey & Pierce, P.L.C.

(57) ABSTRACT

An apparatus for stretching the skin between the fingers of a syndactyly includes first and second upper members, and first and second lower members. Means are provided for adjustably spreading the first and second upper members relative to each other and for adjustably spreading the first and second lower members relative to each other. A first plurality of wires, configured to pierce the skin of the syndactyly and to translate force to bones of the first finger, are connected to the first upper member and to the first lower member. Likewise a similar second plurality of wires are connected to the second upper member and to the second lower member. A method for stretching the skin of the syndactyly includes inserting the first plurality of wires through the skin of the syndactyly between the first and second fingers adjacent the bones of the first finger. The second plurality of wires are inserted similarly adjacent the bones of the second finger. The first plurality of wires is connected to the first upper and lower members, and the second plurality of wires is connected to the second upper and lower members. The first plurality of wires are slowly spread relative to the second plurality of wires such that the first and second plurality of wires spread apart the respective bones of the first and second fingers, thereby stretching the skin of the syndactyly.

17 Claims, 2 Drawing Sheets

FINGER TISSUE EXPANDER

BACKGROUND OF THE INVENTION

1. Field of the Invention

The present invention relates generally to surgical instruments, and relates more particularly to surgical instruments for use in the surgical correction of syndactyly, or webbed fingers.

2. Background of the Art

Syndactyly is a congenital deformity involving fusion of adjacent fingers of the hand. Typically, the bone structure of adjacent fingers is separate, but the skin between the fingers is fused, or webbed. According to prior known techniques, incisions of various configurations have been used to divide the web of skin between the fingers or overlying the fingers. Thereafter, the fingers can be spread apart, and the flaps of skin left by the incisions can be wrapped around each finger, covering as much of each finger as possible. To the extent possible, the free edges of the skin created by the incisions are sutured together where they meet on each finger. Often, however, there is not enough skin to completely cover each finger. In such cases, skin grafts may be employed to complete the skin covering. Disadvantages of the prior techniques include significant scarring, differing texture or color of the skin due to the skin grafts, and complications of healing due to the skin grafts. Functionality of the finger digits may also be compromised where insufficient skin is available, due to tightness of the resulting skin covering.

It would be desirable to provide an improved surgical technique and related apparatus for correcting syndactyly that minimizes the need for skin grafts and that enhances functionality of the finger digits following surgical correction. Such benefits are provided by the present invention.

SUMMARY OF THE INVENTION

According to one aspect of the invention, an apparatus for stretching the skin between first and second fingers of a syndactyly includes first and second upper members and first means for adjustably spreading the first and second upper members relative to each other. Further included are first and second lower members and second means for adjustably spreading the first and second lower members relative to each other. A first plurality of wires are connected to the first upper member and are connected to the first lower member and are configured to pierce the skin of the syndactyly and to translate force to bones of the first finger. A second plurality of wires are connected to the second upper member and are connected to the second lower member and are configured to pierce the skin of the syndactyly and to translate force to bones of the second finger.

According to another aspect of the invention, a method of stretching the skin between first and second fingers of a syndactyly includes the steps of providing a first plurality of wires, and a second plurality of wires. The first plurality of wires are inserted through the skin of the syndactyly between the first and second fingers adjacent the bones of the first finger. The second plurality of wires are inserted through the skin of the syndactyly between the first and second fingers adjacent the bones of the second finger. The first plurality of wires are slowly spread relative to the second plurality of wires such that the first and second plurality of wires spread apart the respective bones of the first and second fingers, thereby stretching the skin of the syndactyly.

It is an object of the present invention to provide an apparatus and method for stretching the skin of a syndactyly prior to surgical separation of the fingers to assure sufficient skin area to cover each finger.

An advantage of the present invention is that syndactylies can be surgically repaired without requiring skin grafts.

Further objects and advantages of the present invention will be apparent from the following description of a preferred embodiment made with reference to the drawings.

DETAILED DESCRIPTION OF THE PREFERRED EMBODIMENT

Figure 1:
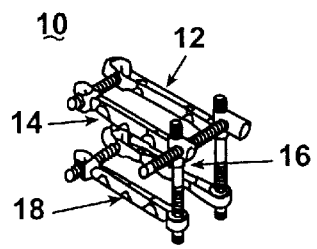
FIG. 1 is a perspective view of a finger tissue expander constructed in accordance with the present invention.
Figure 2:
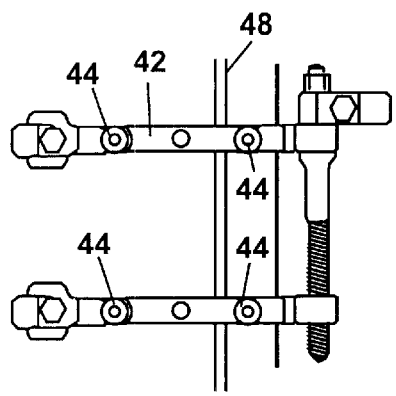
FIG. 2 is an elevation view of the finger tissue expander of FIG. 1.
Figure 3:
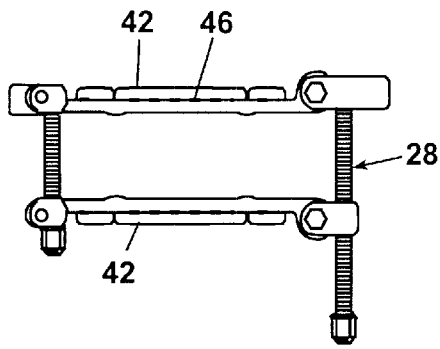
FIG. 3 is a top view of the finger tissue expander of FIG. 1.
Figure 4:
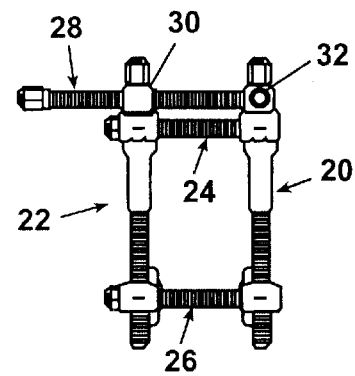
FIG. 4 is a first end view of the finger tissue expander of FIG. 1.
Figure 5:
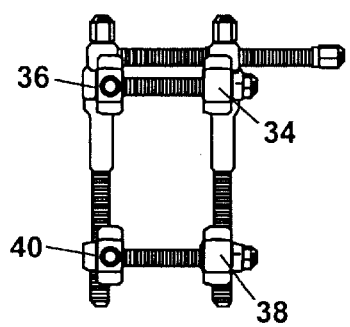
FIG. 5 is a second end view of the finger tissue expander of FIG. 1.

Referring to FIGS. 1–5, a finger tissue expander 10 constructed in accordance with the present invention is illustrated. Finger tissue expander 10 includes as principle components a pair of top moving arms 12 and 14, a pair of bottom moving arms 16 and 18, a pair of vertical adjustment screws 20 and 22, a top rear transverse adjustment screw 24, a bottom rear transverse adjustment screw 26, and a front adjustment screw 28. Vertical adjustment screw 20 is threadedly received through a first end of bottom moving arm 16, and pivotally received through a first end of top moving arm 12. Vertical adjustment screw 22 is threadedly received through a first end of bottom moving arm 18, and pivotally received through a first end of top moving arm 14. Front adjustment screw 28 is threaded received through front swivel 30 and pivotally received in a detent relationship through front click swivel 32. Front swivel 30 is pivotally received on vertical adjustment screw 22, and front click swivel 32 is pivotally received on vertical adjustment screw 20. Top rear transverse adjustment screw 24 is threadedly received through top rear swivel 34 and pivotally received in a detent relationship through top rear click swivel 36. Top rear swivel 34 is pivotally connected to a second end of top moving arm 14, and top rear click swivel 36 is pivotally connected to a second end of top moving arm 12. Bottom rear transverse adjustment screw 26 is threadedly received through bottom rear swivel 38 and pivotally received in a detent relationship through bottom rear click swivel 40. Bottom rear swivel 38 is pivotally connected to a second end of bottom moving arm 18, and bottom rear click swivel 40 is pivotally connected to a second end of bottom moving arm 16. Each of top and bottom rear swivels 34 and 38, and each of top and bottom rear click swivels 36 and 40, are connected to the respective second ends of top and bottom moving arms 14,18,12 and 16 by pins to permit pivoting of swivels 34 and 38 and click swivels 36 and 40 about a vertical axis parallel to that of vertical adjustment screws 20 and 22. Similarly, front swivel 30 and front click swivel 32, pivotally received on vertical adjustment screws 22 and 20, pivot about a vertical axis.

From the above description, it is apparent that the vertical spacing of top moving arms 12 and 14, relative to bottom moving arms 16 and 18, can be varied by turning vertical adjustment screws 20 and 22. The transverse spacing of the second ends of top moving arms 12 and 14 relative to each other can be varied by turning top rear transverse adjustment screw 24. In like manner, the transverse spacing of the second ends of bottom moving arms 16 and 18 relative to each other can be varied by turning bottom rear transverse adjustment screw 26. Finally, the transverse spacing of the first ends of top moving arms 12 and 14, and hence the first ends of bottom moving arms 16 and 18, can be varied relative to each other by turning front adjustment screw 28.

Figure 6:
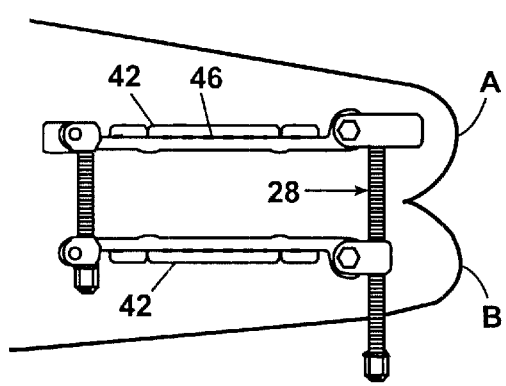
FIG. 6 is a top view of the finger tissue expander of FIG. 1, shown in place relative to a syndactyly.

In use, finger tissue expander 10 would be positioned as shown in FIG. 6, with top moving arms 12 and 14, top rear transverse adjustment screw 24 and front adjustment screw 28 lying above the plane of the hand, and with bottom moving arms 16 and 18 and bottom rear transverse adjustment screw 26 lying below the plane of the hand. Top and bottom moving arms 12, 14, 16 and 18 would lie transversely between and generally parallel to the respective bones of fingers A and B. The first ends of top and bottom moving arms 12,14, 16 and 18 would lie toward the free ends of fingers A and B, whereas the second ends of top and bottom moving arms 12, 14, 16 and 18 would lie toward the junction of fingers A and B with the hand.

Each of top and bottom moving arms 12, 14, 16 and 18 has associated with it a respective cap 42 lying aside the respective moving arm and secured thereto by a pair of screws 44 received freely through holes in cap 42 and threadedly received in threaded holes in the respective moving arm. Each moving arm 12, 14, 16 and 18, and respective cap 42 includes a plurality of vertical grooves 46 on mating faces thereof, each groove 46 having a generally semi-circular cross-section. The grooves 46 on the moving arms 12, 14, 16 and 18 align with the grooves on the respective cap 42 when the moving arm and cap are secured together by screws 44, to define a plurality of vertical through holes having a generally circular cross-section. Received through the vertical through holes formed by grooves 46 are a plurality of stiff wires 48 that are slightly larger in diameter than the through holes. The stiff wires 48 are sandwiched and clamped between the moving arms 12, 14,16 and 18, and the respective cap 42, when screws 44 are tightened.

In use, finger tissue expander 10 is positioned as shown in FIG. 6 and described above relative to the fingers comprising the syndactyly. The front adjusting screw 28 and top and bottom rear transverse adjusting screws 24 and 26 are turned to bring the top moving arms 12 and 14, and the bottom moving arms 16 and 18, sufficiently close together in the transverse direction to lie in planes that pass between the bones of the fingers comprising the syndactyly. Stiff wires 48, each of which is sharpened at one end, are inserted through the through holes formed by the aligned grooves 46 of the top moving arm 12 or 14, pierce through the skin of the syndactyly, and continue through the corresponding through holes formed by the aligned grooves 46 of the bottom moving arm 16 or 18, respectively. As many wires as desired are inserted in this fashion. The process is repeated for the other pair of top and bottom moving arms. Screws 44 are tightened to secure the stiff wires 48 in place. Over time, the adjustment screws 24, 26 and 28 are turned incrementally to slowly spread the moving arms 12, 14, 16 and 18 apart transversely to stretch the skin of the syndactyly. The spreading force generated by the adjustment screws 24, 26 and 28 is transferred to the moving arms 12, 14, 16 and 18 and thence to the stiff wires 48 which bear against the bones of the involved fingers. The detent action of the adjusting screws 24, 26, and 28 relative to the click swivels 36, 40 and 32, provide an audible and tactile indication of the degree of rotation of the adjusting screws 24, 26 and 28. This permits accurate incremental turning of the adjustment screws 24, 26 and 28 and hence well determined incremental stretching of the skin of the syndactyly. After the skin has been stretched sufficiently to provide sufficient surface area to assure coverage of the fingers, the stiff wires 48 are withdrawn and apparatus 10 is removed from the hand. The skin is then incised, wrapped about each finger, and sutured according to known surgical techniques such that the affected fingers are separated and each is fully covered with skin without requiring skin grafts.

Figure 7:
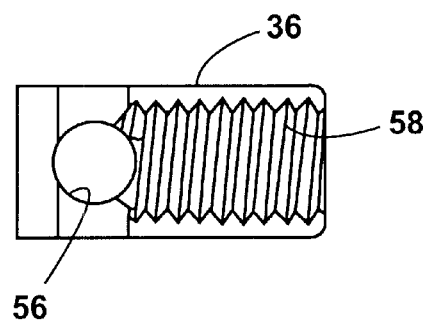
FIG. 7 is a cross-sectional view of a click swivel component of the finger tissue expander of FIG. 1.
Figure 8:
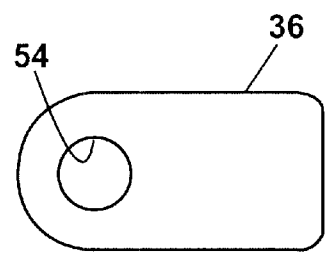
FIG. 8 is a top view of a click swivel component of the finger tissue expander of FIG. 1.
Figure 9:
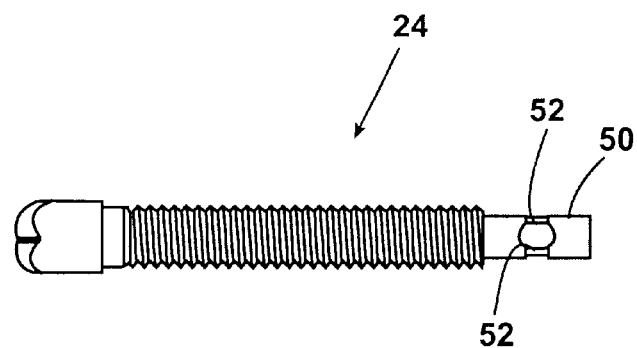
FIG. 9 is a top view of an adjusting screw of the finger tissue expander of FIG. 1.

Referring to FIGS. 7, 8 and 9, the detent mechanism of the adjusting screw 24 and the click swivel 36 is illustrated in greater detail. The detent mechanisms of adjusting screws 26 and 28, and click swivels 40 and 32, respectively, are substantially similar. Adjusting screw 24 has a free end 50 having a substantially round cross section interrupted by a plurality of transverse cylindrical bottomed cuts 52 of substantially equal depth and evenly spaced circumferentially about free end 50 to form four discrete detent stops spaced at 90 degree angles. Click swivel 36 includes a vertical through hole 54 for receiving a pivot pin for pivotally connecting click swivel 36 to the second end of moving arm 12 for pivoting about a vertical axis. Click swivel 36 further includes a transverse through hole 56 for receiving free end 50 of adjusting screw 24 for free rotation therein. A threaded bore 58 receives a detent ball (not shown) for engaging detent stops 52. A coil spring (not shown) is received within bore 58 between the detent ball and a threaded end plug (not shown) also received in bore 58. The spring biases the detent ball against the detent stops 52, providing audible clicks and tactile feedback as adjusting screw 24 is turned relative to click swivel 36.

We claim:

1. An apparatus for stretching the skin between first and second fingers of a syndactyly, comprising:

first and second upper members, each including a first end and a second end;

first means for adjustably spreading said first ends of said first and second upper members relative to each other and for independently adjustably spreading said second ends of said first and second upper members relative each other;

first and second lower members;

second means for adjustably spreading said first and second lower members relative to each other;

a first plurality of wires connected to said first upper member and connected to said first lower member and configured to pierce the skin of the syndactyly and to translate force to bones of the first finger; and a second plurality of wires connected to said second upper member and connected to said second lower member and configured to pierce the skin of the syndactyly and to translate force to bones of the second finger.

2. The apparatus of claim 1, and further including means for adjustably spacing said first and second upper members relative to said first and second lower members.

3. The apparatus of claim 2, in which said means for adjustably spacing includes a threaded member.

4. The apparatus of claim 1, in which at least one of said first and second means for adjustably spreading includes a threaded member.

5. The apparatus of claim 1, in which each of said first and second upper members includes a movable arm and a respective cap and means for affixing said cap to said movable arm, and in which said first and second plurality of wires, respectively, are clamped between said cap and said movable arm.

6. The apparatus of claim 1, in which each of said first and second lower members includes a movable arm and a respective cap and means for affixing said cap to said movable arm, and in which said first and second plurality of wires, respectively, are clamped between said cap and said movable arm.

7. The apparatus of claim 1, in which each of said first and second upper members includes a movable arm having said first end and said second end, and said first means for adjustably spreading said first and second upper members includes means for spreading said first ends of said movable arms relative to each other, and independent means for spreading said second ends of said movable arms relative to each other.

8. The apparatus of claim 1, in which each of said first and second lower members includes a movable arm having a first end and a second end, and said second means for adjustably spreading said first and second lower members includes means for spreading said first ends of said movable arms relative to each other, and independent means for spreading said second ends of said movable arms relative to each other.

9. The apparatus of claim 1, wherein said first and second upper members are operably interconnected with one another by said adjustment mechanism, said first and second lower members are operably interconnected with one another by said adjustment mechanism, said first plurality of wires extending between said first upper member and said first lower member, and said second plurality of wires extending between said second upper member and said second lower member.

10. A method of stretching the skin between first and second fingers of a syndactyly, comprising the steps of:
   providing a first plurality of wires, and a second plurality of wires;
   inserting said first plurality of wires through the skin of the syndactyly between the first and second fingers adjacent bones of the first finger;
   inserting said second plurality of wires through the skin of the syndactyly between the first and second fingers adjacent bones of the second finger; and
   slowly spreading said first plurality of wires relative to said second plurality of wires;
   whereby said first and second plurality of wires spread apart respective bones of the first and second fingers, thereby stretching the skin of the syndactyly.

11. The method of claim 10, and further including the steps of:
   providing first and second upper members and first and second lower members;
   connecting said first plurality of wires to said first upper member and to said first lower member;
   connecting said second plurality of wires to said second upper member and to said second lower member;
   spreading said first and second upper members relative to each other; and
   spreading said first and second lower members relative to each other.

12. The method of claim 10, further comprising the steps of:
   providing an expansible frame;
   connecting said first and second pluralities of wires to said expansible frame for relative movement therebetween; and
   selectively expanding said expansible frame for slowly spreading said first plurality of wires relative to said second plurality of wires.

13. An apparatus for stretching skin covering first and second adjacent bones, comprising:
   an expansible frame including first and second upper members and first and second lower members, each said member including a first end and a second end;
   an adjustment mechanism for selectively,expanding said expansible frame and independently adjusting respective pairs of said first end and said second end of said members relative each other;
   a first plurality of wires extending across a first side of said expansible frame and configured to pierce the skin for applying a force to the first bone;
   a second plurality of wires extending across a second side of said expansible frame, adjacent said first side, and configured to pierce the skin for applying a force to the second bone.

14. The apparatus of claim 13, wherein said adjustment mechanism comprises first and second components for adjustably spacing said first upper member and said first lower member from said second upper member and said second lower member.

15. The apparatus of claim 14, wherein said adjustment mechanism further comprises third and fourth components for adjustably spacing said first and second upper members from said first and second lower members.

16. The apparatus of claim 15, wherein said third and fourth components are threaded members.

17. The apparatus of claim 14, wherein said first and second components are threaded members.

* * * * *

UNITED STATES PATENT AND TRADEMARK OFFICE
CERTIFICATE OF CORRECTION

PATENT NO.   : 6,508,817 B1
DATED        : January 21, 2003
INVENTOR(S)  : Jay M. Pensler, Norris C. Carroll and Brian S. Schumacher It is certified that error appears in the above-identified patent and that said Letters Patent is hereby corrected as shown below:

Column 2,
Line 49, "threaded" should be -- threadedly --.

Column 4,
Line 52, after "relative" insert -- to --.

Column 6,
Line 33, after "relative" insert -- to --.

Signed and Sealed this

Twelfth Day of August, 2003

JAMES E. ROGAN
*Director of the United States Patent and Trademark Office*